(12) United States Patent
Brandt et al.

(10) Patent No.: US 8,887,373 B2
(45) Date of Patent: Nov. 18, 2014

(54) VESSEL SEALING INSTRUMENT WITH REDUCED THERMAL SPREAD AND METHOD OF MANUFACTURE THEREFOR

(75) Inventors: Kim V. Brandt, Loveland, CO (US); Allan G. Aquino, Longmont, CO (US)

(73) Assignee: Covidien LP, Mansfield, MA (US)

( * ) Notice: Subject to any disclaimer, the term of this patent is extended or adjusted under 35 U.S.C. 154(b) by 453 days.

(21) Appl. No.: 13/404,435

(22) Filed: Feb. 24, 2012

(65) Prior Publication Data

US 2013/0226177 A1 Aug. 29, 2013

(51) Int. Cl.
*B23P 15/00* (2006.01)

(52) U.S. Cl.
USPC .......................................... 29/527.4

(58) Field of Classification Search
CPC ............................. A61B 2017/00526
USPC ............................ 606/52; 29/527.4
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| 5,891,142 A * | 4/1999 | Eggers et al. ............ 606/51 |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |

(Continued)

FOREIGN PATENT DOCUMENTS

| | | |
|---|---|---|
| CA | 2590520 | 11/2007 |
| CN | 201299462 | 9/2009 |

(Continued)

OTHER PUBLICATIONS

U.S. Appl. No. 08/926,869, filed Sep. 10, 1997, James G. Chandler.

(Continued)

*Primary Examiner* — Robert N Wieland

(57) ABSTRACT

An electrosurgical vessel sealing instrument having a first and a second opposing jaw member at a distal end thereof, wherein each jaw member includes a jaw housing, a seal plate having a tissue contacting surface and a side wall, and an insulating region disposed on the side wall of the seal plate. The instrument includes the ability to move the jaw members relative to one another from a first position wherein the jaw members are disposed in spaced relation relative to one another to a second position wherein the jaw members cooperate to grasp tissue. The insulating region enables precision overmolding of the jaw housing to the seal plate, while advantageously reducing thermal spread and edge cutting during vessel sealing procedures.

7 Claims, 18 Drawing Sheets

(56) References Cited

U.S. PATENT DOCUMENTS

| | | |
|---|---|---|
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| 7,147,638 B2 | 12/2006 | Chapman et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al |
| D545,432 S | 6/2007 | Watanabe |
| D547,154 S | 7/2007 | Lee |
| 7,270,664 B2 | 9/2007 | Johnson et al. |
| 7,276,068 B2 | 10/2007 | Johnson et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| 7,435,249 B2 | 10/2008 | Buysse et al. |
| D582,038 S | 12/2008 | Swoyer et al. |
| 7,491,202 B2 | 2/2009 | Odom et al. |
| 7,708,735 B2 | 5/2010 | Chapman et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,731,717 B2 | 6/2010 | Odom et al. |
| 7,753,909 B2 | 7/2010 | Chapman et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,877,852 B2 | 2/2011 | Unger et al. |
| 7,877,853 B2 | 2/2011 | Unger et al. |
| 7,922,953 B2 | 4/2011 | Guerra |
| D649,249 S | 11/2011 | Guerra |
| D649,643 S | 11/2011 | Allen, IV et al. |
| 8,112,871 B2 | 2/2012 | Brandt et al. |
| 8,128,624 B2 | 3/2012 | Couture et al. |
| D661,394 S | 6/2012 | Romero et al. |
| 2005/0113826 A1 | 5/2005 | Johnson et al. |
| 2006/0052778 A1 | 3/2006 | Chapman et al. |
| 2006/0217709 A1 | 9/2006 | Couture et al. |
| 2006/0264931 A1 | 11/2006 | Chapman et al. |
| 2007/0074807 A1 | 4/2007 | Guerra |
| 2007/0255279 A1 | 11/2007 | Buysse et al. |
| 2008/0039835 A1 | 2/2008 | Johnson et al. |
| 2008/0045947 A1 | 2/2008 | Johnson et al. |
| 2008/0195093 A1 | 8/2008 | Couture et al. |
| 2009/0062794 A1 | 3/2009 | Buysse et al. |
| 2009/0082766 A1 | 3/2009 | Unger et al. |
| 2009/0082767 A1 | 3/2009 | Unger et al. |
| 2009/0082769 A1 | 3/2009 | Unger et al. |
| 2009/0131934 A1 | 5/2009 | Odom et al. |
| 2009/0204114 A1 | 8/2009 | Odom |
| 2010/0016857 A1 | 1/2010 | McKenna et al. |
| 2010/0179545 A1 | 7/2010 | Twomey et al. |
| 2010/0204698 A1 | 8/2010 | Chapman et al. |
| 2011/0072638 A1 | 3/2011 | Brandt et al. |
| 2011/0082457 A1 | 4/2011 | Kerr et al. |
| 2011/0162796 A1 | 7/2011 | Guerra |
| 2011/0178519 A1 | 7/2011 | Couture et al. |
| 2011/0184405 A1 | 7/2011 | Mueller |
| 2011/0270251 A1 | 11/2011 | Horner et al. |
| 2012/0059371 A1 | 3/2012 | Anderson et al. |

FOREIGN PATENT DOCUMENTS

| | | |
|---|---|---|
| DE | 2415263 | 10/1975 |
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10031773 | 11/2001 |
| DE | 19946527 | 12/2001 |
| DE | 20121161 | 4/2002 |
| DE | 10045375 | 10/2002 |
| DE | 10 2004 026179 | 12/2005 |
| DE | 20 2007 009318 | 8/2007 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| EP | 1486177 | 12/2004 |
| EP | 1527747 | 5/2005 |
| EP | 1632192 | 3/2006 |
| EP | 1685806 | 8/2006 |
| EP | 1707143 | 10/2006 |
| EP | 1946715 | 7/2008 |
| EP | 1958583 | 8/2008 |
| EP | 2103268 | 9/2009 |
| EP | 2147649 | 1/2010 |
| EP | 2301467 | 3/2011 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-10223 | 1/1997 |
| JP | 9-122138 | 5/1997 |
| JP | 10-000195 | 1/1998 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2002-136525 | 5/2002 |

(56) References Cited

FOREIGN PATENT DOCUMENTS

| | | |
|---|---|---|
| JP | 2003-175052 | 6/2003 |
| JP | 2003-245285 | 9/2003 |
| JP | 2004-517668 | 6/2004 |
| JP | 2004-528869 | 9/2004 |
| JP | 2005-253789 | 9/2005 |
| JP | 2006-015078 | 1/2006 |
| JP | 2006-501939 | 1/2006 |
| JP | 2006-095316 | 4/2006 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 02/45589 | 6/2002 |
| WO | WO 02/080786 | 10/2002 |
| WO | WO 2004/098383 | 11/2004 |
| WO | WO 2005/110264 | 11/2005 |
| WO | WO 2006/021269 | 3/2006 |
| WO | WO 2008/040483 | 4/2008 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011 Allan J. Evans.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Homer.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,553, filed Nov. 29, 2011, Duane E. Kerr.
U.S. Appl. No. 13/306,523, filed Nov. 29, 2011, David M. Garrison.
U.S. Appl. No. 13/308,104, filed Nov. 30, 2011, John R. Twomey.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/344,729, filed Jan. 6, 2012, James D. Allen, IV.
U.S. Appl. No. 13/355,829, filed Jan. 23, 2012, John R.Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/360,925, filed Jan. 30, 2012, James H. Orszulak.
U.S. Appl. No. 13/400,290, filed Feb. 20, 2012, Eric R. Larson.
U.S. Appl. No. 13/404,435, filed Feb. 24, 2012, Kim V. Brandt.
U.S. Appl. No. 13/404,476, filed Feb. 24, 2012, Kim V. Brandt.
U.S. Appl. No. 13/412,879, filed Mar. 6, 2012, David M. Garrison.
U.S. Appl. No. 13/412,897, filed Mar. 6, 2012, Joanna Ackley.
U.S. Appl. No. 13/421,373, filed Mar. 15, 2012, John R. Twomey.
U.S. Appl. No. 13/430,325, filed Mar. 26, 2012, William H. Nau, Jr.
U.S. Appl. No. 13/433,924, filed Mar. 29, 2012, Keir Hart.
U.S. Appl. No. 13/448,577, filed Apr. 17, 2012, David M. Garrison.
U.S. Appl. No. 13/460,455, filed Apr. 30, 2012, Luke Waaler.
U.S. Appl. No. 13/461,335, filed May 1, 2012, James D. Allen, IV.
U.S. Appl. No. 13/461,378, filed May 1, 2012, James D. Allen, IV.
U.S. Appl. No. 13/461,397, filed May 1, 2012, James R. Unger.
U.S. Appl. No. 13/461,410, filed May 1, 2012, James R. Twomey.
U.S. Appl. No. 13/464,569, filed May 4, 2012, Duane E. Kerr.
U.S. Appl. No. 13/466,274, filed May 8, 2012, Stephen M. Kendrick.
U.S. Appl. No. 13/467,767, filed May 9, 2012, Duane E. Kerr.
U.S. Appl. No. 13/470,543, filed May 14, 2012, Sean T. Dycus.
U.S. Appl. No. 13/470,775, filed May 14, 2012, James D. Allen, IV.
U.S. Appl. No. 13/470,797, filed May 14, 2012, John J. Kappus.
U.S. Appl. No. 13/482,589, filed May 29, 2012, Eric R. Larson.
U.S. Appl. No. 13/483,733, filed May 30, 2012, Dennis W. Butcher.
U.S. Appl. No. 13/488,093, filed Jun. 4, 2012, Kristin D. Johnson.
U.S. Appl. No. 13/491,853, filed Jun. 8, 2012, Jessica E. Olson.
U.S. Appl. No. 13/537,517, filed Jun. 29, 2012, David N. Heard.
U.S. Appl. No. 13/537,577, filed Jun. 29, 2012, Tony Moua.
U.S. Appl. No. 13/550,322, filed Jul. 16, 2012, John J. Kappus.
U.S. Appl. No. 13/571,055, filed Aug. 9, 2012, Paul Guerra.
U.S. Appl. No. 13/571,821, filed Aug. 10, 2012, Joseph D. Bucciaglia.
U.S. Appl. No. 13/584,194, filed Aug. 13, 2012, Sean T. Dycus.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.

(56) References Cited

OTHER PUBLICATIONS

E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, July 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. " Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05004431.2 dated Jun. 2, 2005.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.

(56) References Cited

OTHER PUBLICATIONS

Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020528.9 dated Aug. 4, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 015215.8 dated Feb. 24, 2010.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175559.3 dated May 25, 2012.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019.9 dated Aug. 22, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 006233.8 dated Feb. 2, 2012.
Int'l Search Report EP 11 007972.0 dated Dec. 28, 2011.
Int'l Search Report EP 11 151509.4 dated Jun. 6, 2011.
Int'l Search Report EP 11 180183.3 dated Nov. 30, 2011.
Int'l Search Report EP 11 152220.7 dated May 19, 2011.
Int'l Search Report EP 11 152360.1 dated Jun. 6, 2011.
Int'l Search Report EP 11 153503.5 dated Mar. 5, 2012.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 168419.7 dated Oct. 20, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report EP 11 180183 dated Nov. 30, 2011.
Int'l Search Report EP 11 183265.5 dated Nov. 28, 2011.
Int'l Search Report EP 11 183476.8 dated Jan. 18, 2012.
Int'l Search Report EP 11 185028.5 dated Jan. 2, 2012.
Int'l Search Report EP 11 189521.5 dated Feb. 20, 2012.
Int'l Search Report EP 11 190723.4 dated Mar. 16, 2012.
Int'l Search Report EP 12 155726.8 dated May 25, 2012.
Int'l Search Report EP 12 155728.4 dated Jul. 4, 2012.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

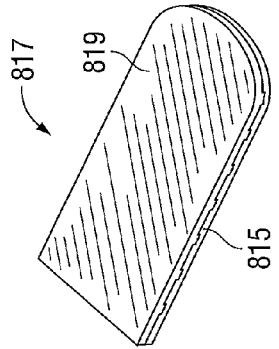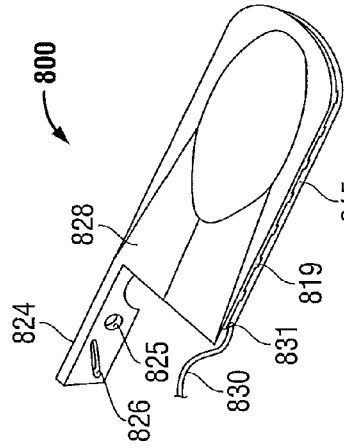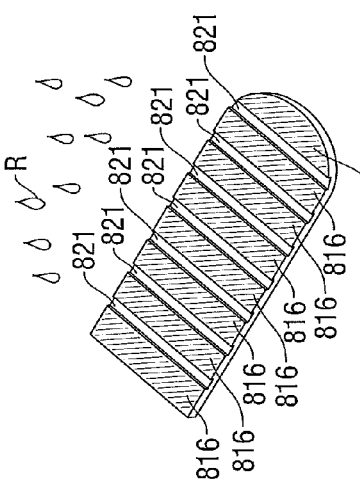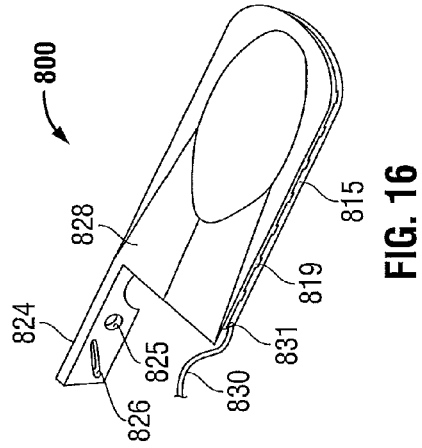

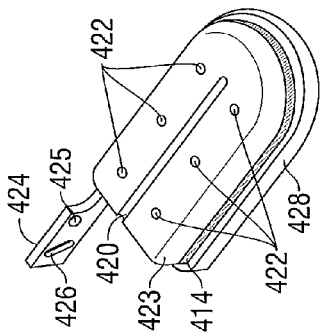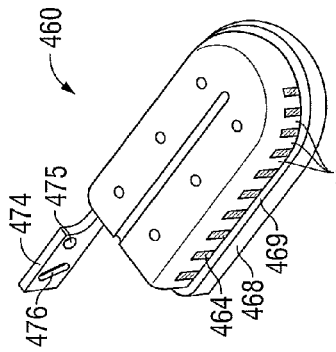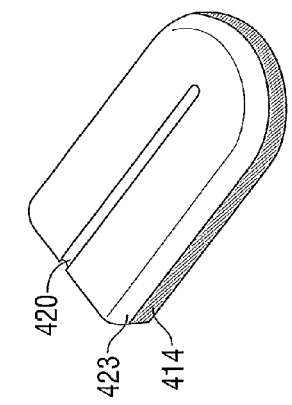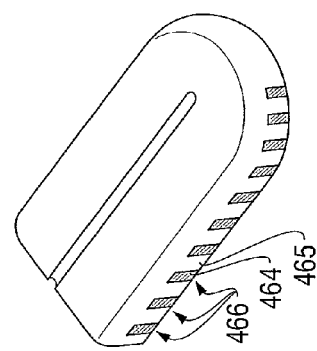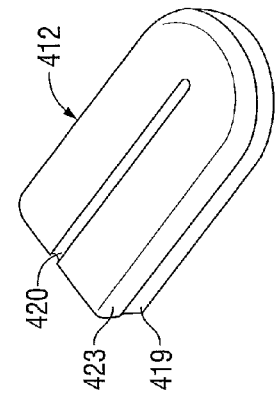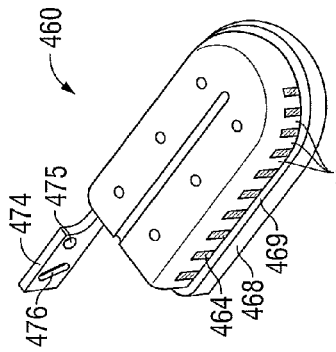

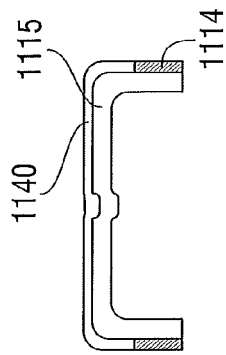
FIG. 37
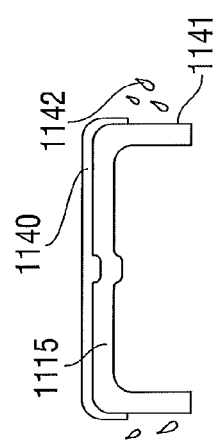
FIG. 36
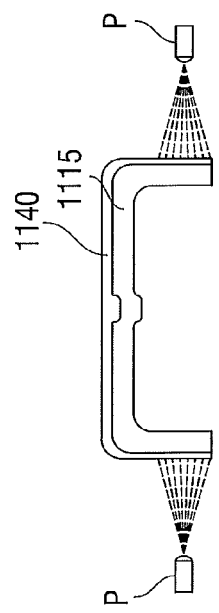
FIG. 35
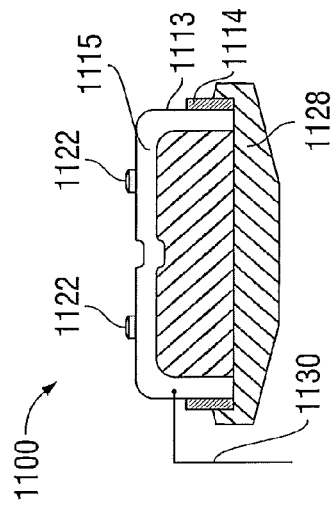
FIG. 40
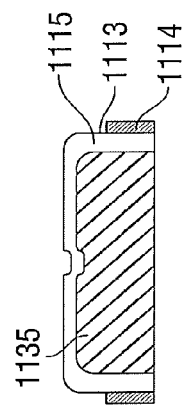
FIG. 39
FIG. 38

ABSTRACT

VESSEL SEALING INSTRUMENT WITH REDUCED THERMAL SPREAD AND METHOD OF MANUFACTURE THEREFOR

BACKGROUND

1. Technical Field

The present disclosure relates to electrosurgical instruments and methods for performing surgical procedures and, more particularly, to an electrosurgical vessel sealing instrument with a jaw assembly having one or more insulating members associated with the sealing plate that provide reduced thermal spread and reduced edge cutting while enabling improved dimensional tolerances during the prototyping and manufacturing process.

2. Background of Related Art

A hemostat or forceps is a simple pliers-like tool that uses mechanical action between its jaws to constrict tissue and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize and/or seal vascular tissue.

Using electrosurgical forceps, a surgeon can elect to seal, cauterize, coagulate, or desiccate tissue, or simply reduce or slow bleeding by controlling the intensity, frequency and duration of the electrosurgical energy applied to the tissue. Generally, the electrical configuration of electrosurgical forceps can be categorized in two classifications: 1) monopolar electrosurgical forceps; and 2) bipolar electrosurgical forceps.

Monopolar forceps utilize one active electrode associated with the clamping end effector and a remote patient return electrode or pad that is attached externally to the patient, e.g., on the leg or buttocks. When electrosurgical energy is applied, the energy travels from the active electrode, to the surgical site, through the patient, and to the return electrode.

Bipolar electrosurgical forceps utilize two generally opposing electrodes that are generally disposed on the inner facing or opposing surfaces of the end effectors (e.g., jaws of the instrument) which are, in turn, electrically coupled to an electrosurgical generator. Each electrode is charged to a different electric potential. Since tissue is a conductor of electrical energy, when the end effectors are utilized to clamp or grasp tissue therebetween, the electrical energy can be selectively transferred through the tissue to cause a change therein and effect sealing of the vessel.

Certain surgical procedures require sealing blood vessels or vascular tissue. The term "vessel sealing" is defined as the process of liquefying the collagen in the tissue so that the tissue cross-links and reforms into a fused mass. In order to form a burst-resistant and sound vessel seal, the application of sealing energy should be targeted to the specific region of tissue to be sealed. Excessive thermal energy should not be allowed to spread to adjacent areas of tissue, as this may diminish the integrity of a resulting seal since the energy required to form the seal is dissipated into the surrounding tissue rather than into the region intended to be sealed. For the purposes herein the term "thermal spread" refers generally to the heat transfer (heat conduction, heat convection or electrical current dissipation) dissipating along the periphery of the electrically conductive or electrically active surfaces of an electrosurgical instrument to adjacent tissue. This can also be termed "collateral damage" to adjacent tissue. One form of collateral damage is referred to as "edge cutting" whereby current concentrations near the edge of the electrode partially or completely sever the vessel being sealed. The reduction and control of such thermal spread and attendant collateral damage is therefore a desirable objective in the design of a vessel sealing instrument.

SUMMARY

The present disclosure relates to an electrosurgical vessel sealing instrument having a seal plate disposed on the opposing faces of the vessel-sealing jaws. It has been found that reducing the height of the seal plate side walls may minimize thermal spread, yet, too much of a reduction in sidewall height may result in excessive current concentrations resulting in increased edge cutting. Therefore, seal plate height must be precisely controlled in order to achieve optimum performance, e.g., minimal thermal spread with minimal edge cutting. The vertical dimension of the seal plate is determined at least in part by the manufacturing process used to form the jaw member. Using prior art overmolding techniques, it is difficult to maintain the tolerances necessary to form a jaw member having the desired minimal thermal spread and minimal edge cutting properties since variations in edge height were unavoidable. During product development cycles, where numerous and different prototypes may be built, the overmolding process may not be cost-effective and may yield unsatisfactory results, particularly when a prototype jaw member needs to be fabricated precisely for evaluation purposes.

In some embodiments, a seal place in accordance with the present disclosure includes an obverse tissue-contacting sealing surface, a reverse surface, and a surrounding side wall defining an edge therebetween. The side walls of the seal plate incorporate one or more insulators that precisely define the shutoff depth, e.g., a line describing a delineation on the side wall between the conductive and non-conductive portions of the seal plate. An insulator may be disposed within a recess or groove formed along a side wall of the seal plate. An insulator may be continuously disposed along a side wall of the seal plate or may be discontinuously disposed, e.g., in a notched, dentil, or other suitable pattern. An insulator according to the present disclosure may be flush with a surface of the seal plate, or alternatively may protrude from the surface of the seal plate, may be recessed into the surface of the seal plate, or may be disposed upon the surface of the seal plate. The groove, notches, or other recesses disposed within the seal plate may be formed by photolithography.

In an embodiment, a reverse surface of the seal plate includes a plurality of ribs and/or valleys defined thereupon. An insulating layer having an obverse side and a reverse side is intimately and conformally fixed to the seal plate mounting surface such that the valleys and/or ribs of the seal plate reverse surface engage corresponding features of the insulator obverse face. An edge of the seal plate defined by the sealing surface and the side wall is radiused. The ribbed pattern of the seal plate and insulator, and the radiused edge of the seal plate provides optimal current paths while minimizing thermal spread and collateral damage, e.g., edge cutting. In some embodiments a base plate is fixed to a reverse face of the insulator to facilitate mounting of the seal plate/insulator to a jaw housing. A reverse face of the base plate may include notched, grooved, or dovetailed features adapted to enhance adhesion between the base plate and the jaw housing.

By the disclosed arrangement, sealing current is uniformly concentrated within the sealing surface of the jaws (e.g., the seal plate) while concurrently providing enhanced electrical and thermal isolation along the side walls of the seal plate. The disclosed arrangement of the electrode insulating material and the electrically conductive sealing surface provides a more consistent, high quality seal and effectively reduces thermal spread to adjacent tissue during use. Preferably, the geometry of the insulating substrate and seal plate also isolates the two electrically opposing electrodes formed by opposing seal plates within a pair of jaws from one another, thereby reducing the possibility that tissue or tissue fluids can create an unintended bridge or path for current travel.

In an embodiment, the disclosed electrosurgical instrument includes a first jaw member and a second opposing jaw member at a distal end thereof. Each jaw member includes a jaw housing, a tissue contacting seal plate, and an insulating layer disposed therebetween attaching the seal plate to the jaw housing. The seal plate includes one or more ribs extending from a reverse surface of the seal plate into the insulating layer. At least one of the jaw members is movable from a first position wherein the jaw members are disposed in spaced relation relative to one another to a second position wherein the jaw members cooperate to grasp vessel tissue therebetween.

Also disclosed is an electrosurgical vessel sealing system. In an embodiment, the disclosed vessel sealing system includes a source of electrosurgical vessel sealing energy adapted to operably couple to an electrosurgical vessel sealing instrument. The electrosurgical instrument includes a first jaw member and a second opposing jaw member at a distal end thereof. Each jaw member includes a jaw housing, a tissue contacting seal plate, and an insulating layer disposed therebetween attaching the seal plate to the jaw housing. The seal plate includes one or more ribs extending from a reverse surface of the seal plate into the insulating layer. At least one of the jaw members is movable from a first position wherein the jaw members are disposed in spaced relation relative to one another to a second position wherein the jaw members cooperate to grasp vessel tissue therebetween.

Also disclosed is an electrosurgical instrument that includes a first jaw member and a second opposing jaw member at a distal end of the electrosurgical instrument. Each jaw member comprises a seal plate having a top tissue contacting surface, and a side wall extending from a peripheral edge of the tissue contacting surface wherein the side wall includes an outer surface and a bottom edge. An insulator is disposed on an outer surface of the side wall. A jaw is housing fixed to the bottom edge of the side wall and at least a portion of the insulating region. The jaw housing may be formed by any suitable manner of manufacture, for example without limitation, overmolding. At least one of the jaw members is movable from a first position where the jaw members are disposed in spaced relation relative to one another to a second position where the jaw members cooperate to grasp tissue therebetween.

The present disclosure is also directed to a method of manufacturing a jaw member. The disclosed method includes the steps of providing a blank seal plate, applying a resist mask to a reverse surface of the seal plate defining a plurality of valley regions, etching the masked reverse surface of the seal plate to form a plurality of valleys therein defining at least one rib on the reverse surface of the seal plate, removing the resist mask from the seal plate, affixing an insulating layer to the reverse surface of the seal plate, and affixing a reverse surface of the insulating layer to a jaw housing.

Yet another method of manufacturing a jaw member in accordance with the present disclosure includes the steps of forming a raw seal plate having a tissue contacting surface and a side wall. A photoresist material is applied to at least a portion of the raw seal plate to form a coating. A portion of the coating corresponding to an insulating region is exposed to an energy source, e.g., a photolithographic energy source such as without limitation ultraviolet light or electron beam energy. The coating is developed to reveal a region of the side wall corresponding to the insulating region. An insulating material is applied to the region of the side wall corresponding to the insulating region. The remaining coating is removed from the raw seal plate, and a jaw housing is overmolded to a bottom side of the raw seal plate and at least a part of the insulating region. A recessed region may be formed in the side wall corresponding to the insulating region.

Yet another electrosurgical vessel sealing system is disclosed herein that includes a source of electrosurgical vessel sealing energy and an electrosurgical instrument configured to operably couple to the source of electrosurgical energy. The electrosurgical instrument includes a first jaw member and a second opposing jaw member at a distal end of the electrosurgical instrument. Each jaw member comprises a seal plate having a top tissue contacting surface, and a side wall extending from a peripheral edge of the tissue contacting surface wherein the side wall includes an outer surface and a bottom edge. An insulator is disposed on an outer surface of the side wall. A jaw is housing fixed to the bottom edge of the side wall and at least a portion of the insulating region. The jaw housing may be formed by any suitable manner of manufacture, for example without limitation, overmolding. At least one of the jaw members is movable from a first position where the jaw members are disposed in spaced relation relative to one another to a second position where the jaw members cooperate to grasp tissue therebetween.

BRIEF DESCRIPTION OF THE DRAWINGS

Various embodiments of the subject instrument are described herein with reference to the drawings wherein:

FIG. 13 illustrates an example step of a method of manufacturing a jaw member in accordance with the present disclosure wherein a resist mask is removed;

FIG. 14 illustrates an example step of a method of manufacturing a jaw member in accordance with the present disclosure wherein an insulating layer is applied to a surface of a seal plate;

FIG. 15 illustrates an example step of a method of manufacturing a jaw member in accordance with the present disclosure wherein insulating material is removed therefrom;

FIG. 16 illustrates an example step of a method of manufacturing a jaw member in accordance with the present disclosure wherein a jaw housing is overmolded to a seal plate;

FIG. 29 is a perspective view of an example seal plate having a continuous recess in accordance with the present disclosure;

FIG. 30 is a perspective view of the FIG. 29 seal plate having insulating material deposited in the etched recess in accordance with the present disclosure;

FIG. 31 is a perspective view of an example jaw member incorporating the seal plate of FIG. 30 in accordance with the present disclosure;

FIG. 32 is a perspective view of an example seal plate having a series of notched recesses in accordance with the present disclosure;

FIG. 33 is a perspective view of the FIG. 32 seal plate having insulating material deposited in the notched recesses in accordance with the present disclosure;

FIG. 34 is a perspective view of an example jaw member incorporating the seal plate of FIG. 33 in accordance with the present disclosure;

FIG. 35 is a cross-sectional view of another example seal plate having a photoresist coating and undergoing exposure in accordance with the present disclosure;

FIG. 36 is a cross-sectional view of another example seal plate undergoing photoresist developing in accordance with the present disclosure;

FIG. 37 is a cross-sectional view of another example seal plate undergoing insulation application in accordance with the present disclosure;

FIG. 38 is a cross-sectional view of another example seal plate undergoing photoresist removal in accordance with the present disclosure;

FIG. 39 is a cross-sectional view of another example seal plate with a first overmold in accordance with the present disclosure;

FIG. 40 is a cross-sectional view of another example seal plate with a second overmold in accordance with the present disclosure;

DETAILED DESCRIPTION

Figure 1:
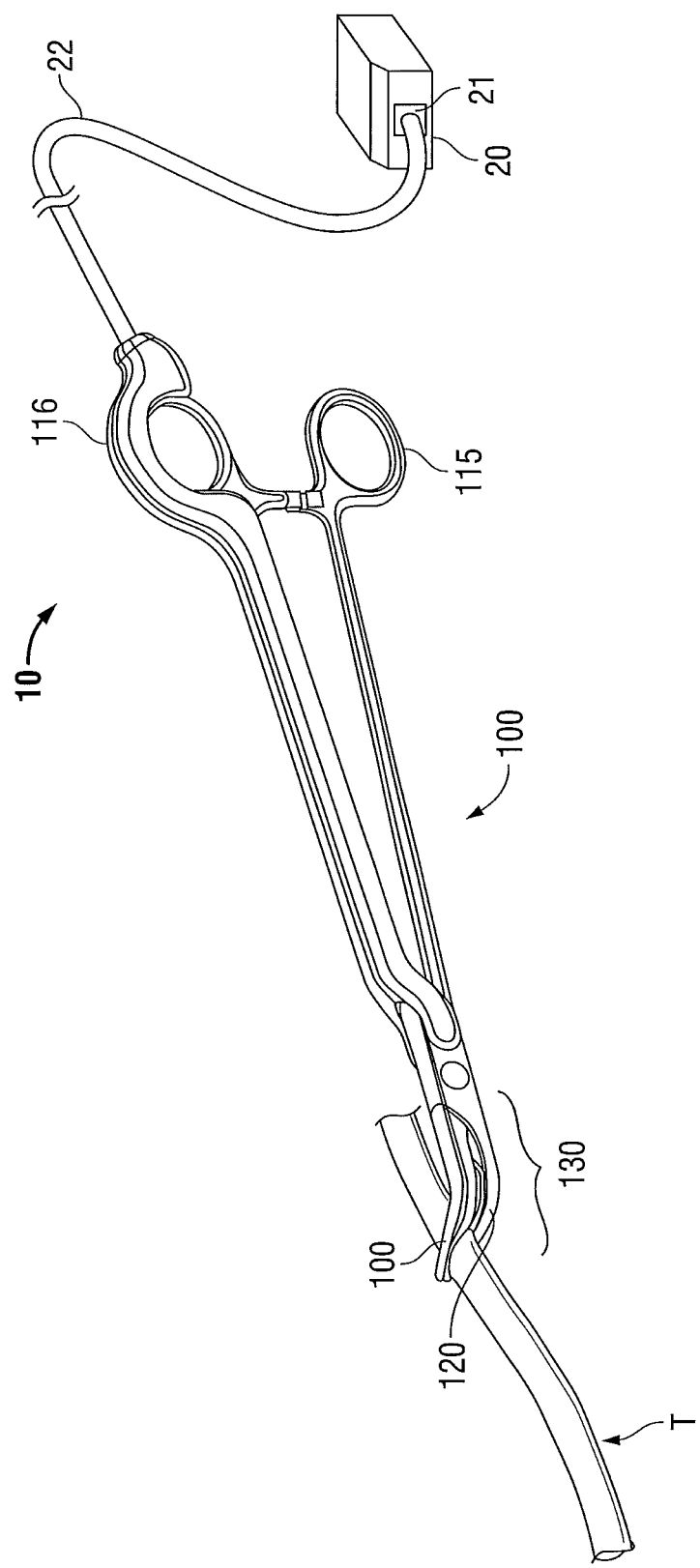
FIG. 1 is a functional view of an example embodiment of a vessel sealing system utilizing a hemostat-style vessel sealing instrument in accordance with the present disclosure.

Particular embodiments of the present disclosure are described hereinbelow with reference to the accompanying drawings; however, the disclosed embodiments are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, shall refer to the end of the instrument that is closer to the user, while the term "distal" shall refer to the end that is farther from the user. The term "obverse" shall refer to a direction facing towards a tissue contacting surface of a jaw member, while "reverse" shall refer to the direction facing away from a tissue contacting surface of a jaw member. In addition, as used herein, terms referencing orientation, e.g., "top", "bottom", "up", "down", "left", "right", "clockwise", "counterclockwise", "upper", "lower", and the like, are used for illustrative purposes with reference to the figures and features shown therein. It is to be understood that embodiments in accordance with the present disclosure may be practiced in any orientation without limitation. In this description, as well as in the drawings, like-referenced numbers represent elements which may perform the same, similar, or equivalent functions.

Referring to FIG. 1, an embodiment of a vessel sealing system 10 in accordance with the present disclosure is shown generally and includes a bipolar forceps 100 having an end effector assembly 130 that includes first and second jaw members 110 and 120 that mutually cooperate to grasp, seal, and/or divide a tubular vessel "T". As shown, handle members 115 and 116 of instrument 100 are of the scissors type; however, any suitable type of handle is envisioned within the scope of the present disclosure. The handle members 115 and 116 offer a surgeon a gripping position from which to grasp forceps 100 and to transmit a clamping pressure to end effector assembly 130. During use, handle members 115 and 116 are moved closer to one another to cause jaw members 110 and 120 to apply a clamping force and electrosurgical energy to the tubular vessel T to effect a tissue seal. Once sealed, the tubular vessel T can be cut along the seal to separate the vessel T leaving two scored ends.

Forceps 100 further includes an electrical cable 22 extending therefrom that couples forceps 100 to a source of electrosurgical energy 20, e.g., a generator 20. In some embodiments, a source of electrosurgical energy, and/or a power source, such as without limitation, a rechargeable battery (not shown), may be included within forceps 100. Cable 22 may couple to generator 20 via connector 21, and is adapted to provide vessel sealing energy to jaw members 110 and 120.

Figure 2:
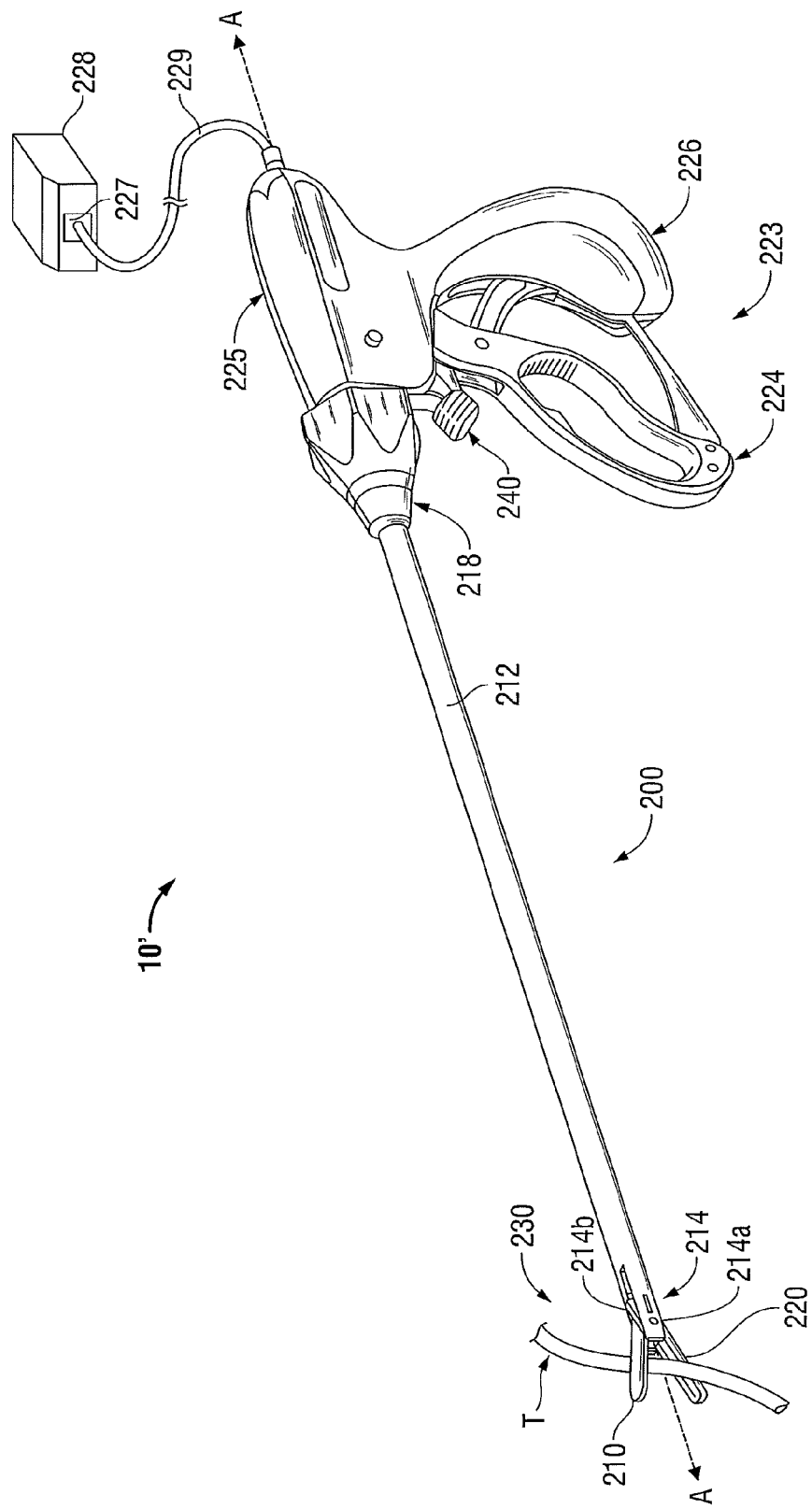
FIG. 2 is a functional view of another example embodiment of a vessel sealing system utilizing a vessel sealing instrument suitable for minimally-invasive procedures in accordance with the present disclosure.

In another example embodiment depicted in FIG. 2, a vessel sealing system 10' includes an endoscopic forceps 200 having a housing 225 including a shaft 212 extending therefrom that enables a surgeon to perform minimally-invasive (e.g., endoscopic or laparoscopic) surgical procedures. Shaft 212 may alternatively have a shorter, or longer, length than that shown in FIG. 2, which may be desirably utilized in various endoscopic and/or open surgical procedures. Rotating assembly 218 is attached to a distal end of housing 225 and is rotatable in either direction about a longitudinal axis "A-A" defined through the shaft 212. In some embodiments, rotating assembly 218 is rotatable approximately 180 degrees in either direction about the longitudinal axis "A-A". Rotation of rotating assembly 218 correspondingly rotates end effector assembly 230 about the longitudinal axis "A-A" to facilitate manipulation of tissue. In some embodiments, shaft 212 is bifurcated at a distal end 214 thereof to form ends 214a and 214b, which are configured to receive end effector assembly 230.

Housing 225 is formed from two housing halves that engage one another via a series of mechanical interfaces to form an internal cavity for housing the internal working components of instrument 10'. For the purposes herein, the housing halves are generally symmetrical and, unless otherwise noted, a component described with respect to a first of the housing halves will have a similar component which forms a part of a second of the housing halves.

Handle assembly 223 includes a first handle 226 and a second handle 224. End effector assembly 230 is attached to distal end 214 of shaft 212 and includes a pair of opposing jaw members 210 and 220. Second handle 224 is selectively movable about a pivot (not explicitly shown) from a first position in spaced relation relative to first handle 226 to a second position in closer proximity relative to first handle 226, which, in turn, imparts movement of jaw members 210 and 220 relative to one another, e.g., from an open to closed position about tissue T. For illustrative purposes, jaw member 210 may be referred to as an upper jaw member 210 and jaw member 220 may be referred to as a lower jaw member 220. First and second handles 226, 224 are ultimately connected to a drive assembly (not explicitly shown) which, together, mechanically cooperate to impart movement of jaw members 210, 220 from an open position wherein the jaw members 210, 220 are disposed in spaced relation relative to one another, to a clamping or closed position wherein, e.g., jaw members 210, 220 cooperate to grasp tissue T therebetween and to deliver electrosurgical energy to tissue T.

Forceps 200 further includes an electrical cable 229 extending from housing 225 which couples instrument 200 to a source of electrosurgical energy, e.g., a generator 228. Cable 229 may couple to generator 228 via connector 227, and is adapted to provide vessel sealing energy to jaw members 210 and 220.

Jaw members 210, 220 may be electrically isolated from one another such that electrosurgical energy can be effectively transferred through the tissue disposed therebetween to form the seal.

End effectors 130 and/or 230 may additionally or alternatively be curved in order to reach specific anatomical structures. For example, dimensioning end effectors 130 and/or 230 at an angle of about 50° to about 70° is preferred for accessing and sealing specific anatomical structures, e.g., those anatomical structures relevant to prostatectomies and cystectomies, such as without limitation the dorsal vein complex and the lateral pedicles.

Figure 3:
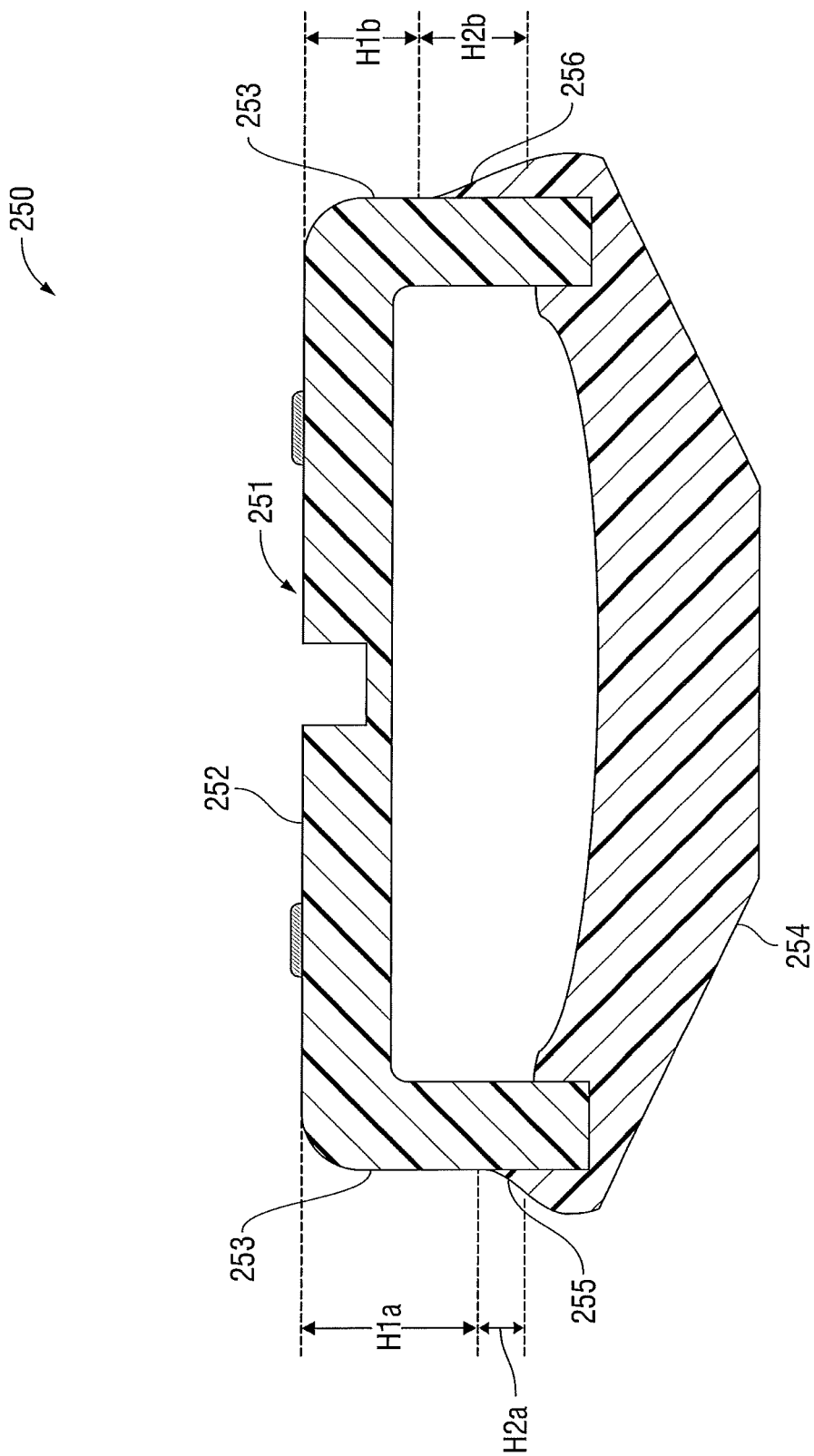
FIG. 3 is a cross-sectional view of a prior art jaw member.

FIG. 3 illustrates a cross-sectional view of prior art jaw member 250. Prior art jaw member 250 includes a seal plate 251 having a tissue-contacting surface 252 and sides walls 253. The side walls 253 are embedded in a jaw housing 254 that can be formed by overmolding. The shutoff height, i.e., the height of the exposed conducive surface of the side wall 253 is denoted by H1$a$ on the left and H1$b$ on the right. As demonstrated in FIG. 3, flashing 255 and 256 from the overmolding process remains disposed upon the side walls 253. As can be appreciated, due to the limitations of the overmolding process, the amount of flashing may vary considerably around the junction of seal plate 251 and jaw member 254. In the example prior art jaw member 250 presented in FIG. 3, flashing 255 extends slightly up the left sidewall 253 over a length denoted by H2$a$, while, on the opposite side, flashing 256 extends further up the right sidewall 256 over a length denoted by H2$b$. These manufacturing variations result in a left side shutoff distance H1$a$ being greater than right side shutoff distance H1$b$. During use, these differences in shutoff dimension may contribute to unbalanced or uneven sealing and/or may contribute to collateral tissue damage, since the manufactured shutoff dimensions vary from the intended design dimension and cause uneven or suboptimal delivery of energy to tissue.

While in theory the overmolding process may be modified to reduce flashing in the prior art design, in practice, the required modifications may result in lower production yields, require longer manufacturing times, be more labor-intensive, may require more expensive processes and/or tooling, and generally are not cost effective.

Figure 4:
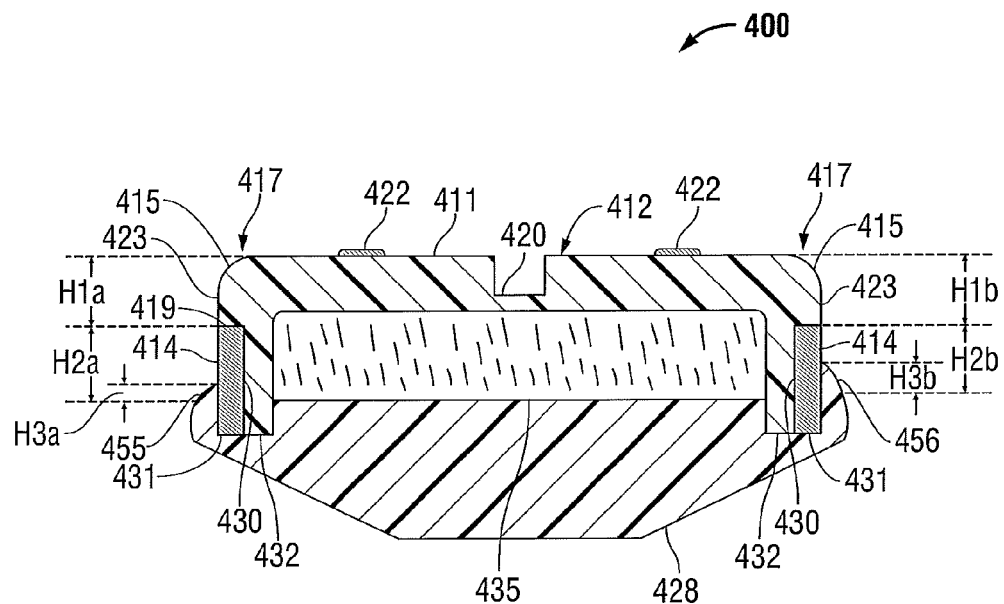
FIG. 4 is a cross-sectional view of an example embodiment of a jaw member that includes a flush-mounted insulating shutoff incorporated in the side wall of the seal plate in accordance with the present disclosure.

Turning now to FIG. 4, an example embodiment of a jaw member 400 in accordance with the present disclosure is described in detail. The described features of jaw member 400 are representative of one or more of the jaw members as described hereinabove (e.g., jaw members 110 and 120 of FIG. 1 and/or jaw members 210 and 220 of FIG. 2), and when included in an end effector assembly having opposing jaws (e.g., end effector assembly 130 of FIG. 1 and/or end effector assembly 230 of FIG. 2) include mutually corresponding component features that cooperate to permit rotation about a pivot pin (not explicitly shown) to effectively grasp, seal, and/or divide tissue.

Jaw member 400 includes an electrically conductive electrode or seal plate 412 having a tissue-contacting surface 411 and side walls 423. As shown, seal plate 412 has a generally inverted U-shaped cross section; however, seal plates in accordance with the present disclosure are not limited to the inverted U-shape shown herein. Seal plate 412 may be formed by any suitable manner of formation, including without limitation, stamping, casting, machining, and the like. A knife slot 420 may be defined in the tissue-contacting surface 411 of seal plate 412. Tissue-contacting surface 411 of seal plate 412 has a perimetric edge 417 that includes a radius 415. In some embodiments, radius 415 has a radius of about 0.05". One or more stop members 422 are disposed upon a surface 411 and are configured to limit the minimum clearance between jaw members during use to within a specified range, typically about 0.001" to about 0.006". Each stop member 422 is made from an insulative material.

As seen in FIGS. 4, 9, and 29-31, a groove 419 is defined along an outer side wall 423 of seal plate 412. In the FIG. 4 embodiment, groove 419 runs longitudinally around side wall 423 and extends downward to a bottom surface 431 of side wall 423. An insulator 414 is disposed within groove 419. Insulator 414 may be formed form any suitable high-temperature, biocompatible material, including without limitation polyimide. An inner support 435 is included within seal plate 412 that is adapted to provide additional strength and rigidity to the jaw member 400. In some embodiments, inner support 435 may be formed from polyphthalamide (PPA) thermoplastic polymer, such as Amodel® manufactured by Solvay Advanced Polymers of Alpharetta, Ga., United States. Inner support 435 may be formed by any suitable method of manufacture, including without limitation, overmolding.

Jaw member 400 includes a jaw housing 428 that is fixed to a reverse end 432 of side walls 423 and/or inner support 435. Jaw housing 428 supports the combination of seal plate 412 and inner support 435. In some embodiments, jaw housing 428 may be formed from non-conductive material, such as without limitation, high-strength ceramic material, and may be formed by overmolding. Jaw housing 428 may include a number of features designed to facilitate the mounting thereof on an instrument, e.g., a hinge plate 424 extending from a proximal end thereof. (See FIG. 31.) The hinge plate 424 may include additional features adapted to pivot, mount, and articulate jaw member 400, including without limitation, pivot hole 425 and/or cam slot 426. A conductor (not explicitly shown) operably couples seal plate 412 to a source of vessel sealing energy, e.g., generators 20, 228.

The configuration of jaw member 400 enables the shutoff height H1a, H1b to be consistently defined despite variations in tolerance, e.g., flashing, which is a byproduct of the overmolding process. As can be seen in FIG. 4, the left side of jaw housing 428 includes a flashing region 455 having a height H3a, while the right side of jaw housing exhibits flashing 456 that extends further upward (denoted as H3b) than does flashing 455. Advantageously, the shutoff height H1a and H1b of disclosed jaw member 400 is determined by the top edge 419 of insulator 414, not by the imprecise top edges 455, 456 of jaw housing 428. Thus, a consistent shutoff height is achieved by a jaw member 400 in accordance with the present disclosure despite dimensional variances that may result from overmolding, or other suitable manufacturing processes.

Turning now to FIGS. 32-34, another embodiment of a jaw member 460 according to the present disclosure is illustrated wherein one or more notches 469 are defined in an outer surface 461 of side wall 463 and having an insulator 464 disposed therein to form a series of one or more insulating regions 466. A jaw housing 468 is joined to seal plate assembly 462 as described hereinabove. A portion of each insulating region 464 extends beyond an overmolded region 469 of jaw housing 468 to form an alternating series of conductive regions 465. It is believed that the described arrangement of conductive regions 465 may influence current paths within and around seal plate 462 that consequently reduce the incidence of collateral tissue damage, e.g., edge cutting and thermal spread. As shown, the width of an insulating region 464 and a conductive region 465 is about equal, e.g., about 1:1; however, in some embodiments the ratio of insulating region width to conductive region width may range from about 1:5 to about 5:1, and can be in a range of about 1:100 to about 100:1. This ratio may vary along the edge(s) of a seal plate, such that, for example and without limitation, the width of successive insulating regions increases or decreases as viewed across the face of a seal plate side wall.

Figure 5:
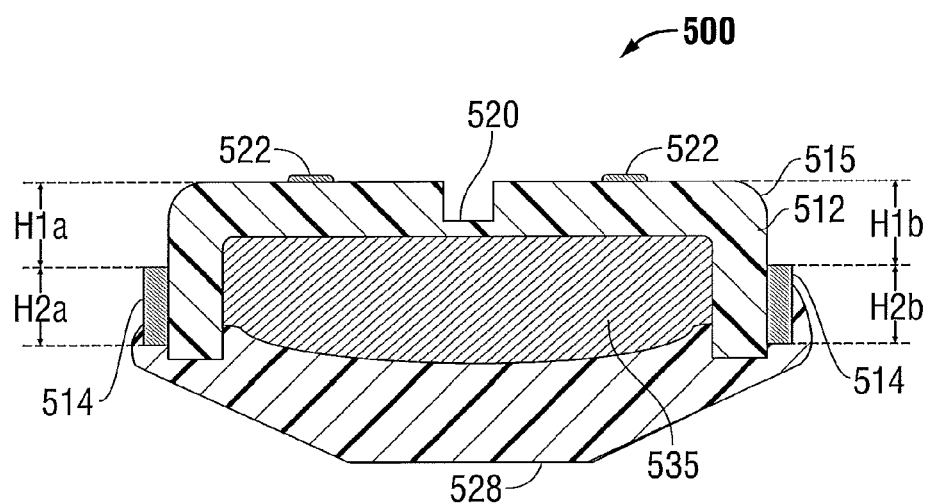
FIG. 5 is a cross-sectional view of another example embodiment of a jaw member that includes a surface-mounted insulating shutoff disposed on the side wall of the seal plate in accordance with the present disclosure.
Figure 41:
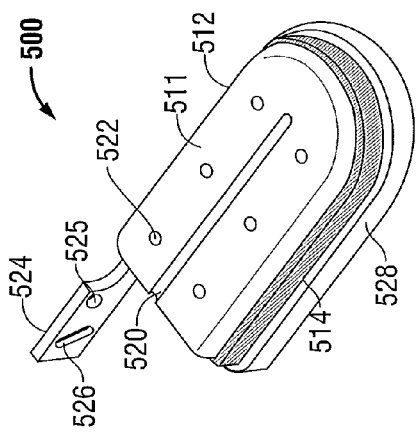
FIG. 41 is a perspective view of another example seal plate having a continuous surface-mounted insulator in accordance with the present disclosure.
Figure 42:
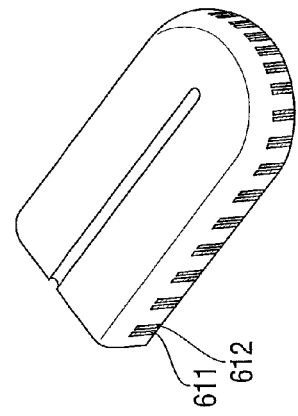
FIG. 42 is a perspective view of another example jaw member incorporating the seal plate of FIG. 41 in accordance with the present disclosure.

Turning now to FIGS. 5, 41, and 42, yet another embodiment of a jaw member 500 in accordance with the present disclosure is presented wherein a seal plate 512 includes an insulating band 514 disposed around a periphery thereof. Insulating band 514 may be formed from any suitable heat resistant and biocompatible material, such as without limitation, polyimide. Insulating band 514 may be overmolded, formed from heat shrink material, applied using photoresistive mask, and the like. Jaw member 500 includes a seal plate support 535 that may be formed from PPA, and a jaw housing 535 that may be formed by overmolding, as previously discussed. One or more stop members 522 are disposed upon a surface 511 of seal plate 512 and are configured to limit the minimum clearance between jaw members, as discussed above.

FIGS. 43-48 illustrate additional example embodiments of a seal plate in accordance with the present invention. In particular, several envisioned alternative arrangements of peripheral insulating regions are disclosed. It is believed that by varying the widths of the insulating regions and/or the conductive regions around the periphery of the seal plate, collateral damage may be managed in a controlled manner. Certain arrangements of insulating regions, for example, may deliver sealing energy in a manner best suited for certain types of tissue. In some embodiments, the insulation pattern may enable the precise delivery of edge energy which may, in turn, allow procedures in proximity to sensitive anatomical structures, which would have been ill-advised with prior-art instruments, to be successfully performed.

Figure 44:
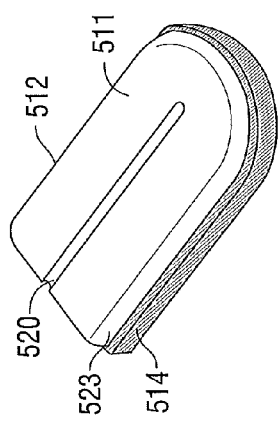
FIG. 44 is a perspective view of yet another example seal plate having a plurality of insulators in a staggered arrangement in accordance with the present disclosure.
Figure 43:
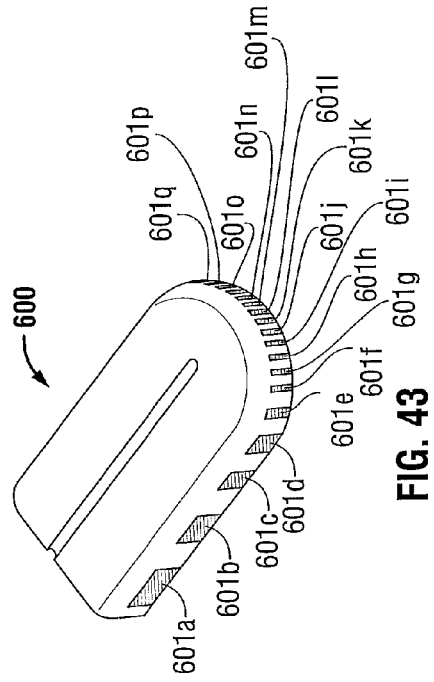
FIG. 43 is a perspective view of another example seal plate having a plurality of insulators of varying width in accordance with the present disclosure.
Figure 48:
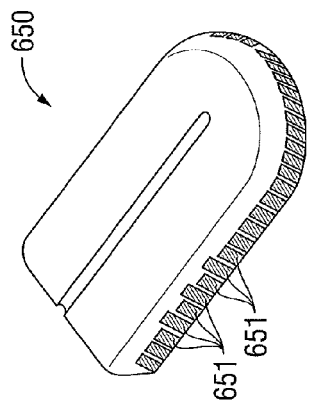
FIG. 48 is a perspective view of still another additional example of a seal plate having a plurality of insulators of varying height in accordance with the present disclosure.

For example, in FIG. 43 a seal plate having a series of insulating regions 601 et seq., each having a successively decreasing width is shown. At a proximal end the insulating regions 601a, 601b, 601c et seq. are wider and at a distal end insulators 601k et seq. are narrower. In FIG. 44, seal plate 610 includes a series of staggered insulating regions 611, 612. FIGS. 45-48 illustrate various alternative insulator configurations: diagonal (FIG. 45), increasing/decreasing (FIG. 46), sawtooth or triangular (FIG. 47), and varying height (FIG. 48). It is to be understood that these are merely example insulating region configurations, and a seal plate in accordance with the present disclosure may have variation and combinations of these and other insulator configurations.

Figure 18:
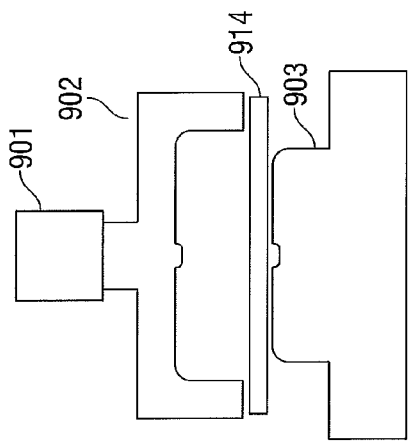
FIG. 18 illustrates an example step of a method of manufacturing a jaw member in accordance with the present disclosure wherein a seal plate blank is positioned in a forming die.
Figure 20:
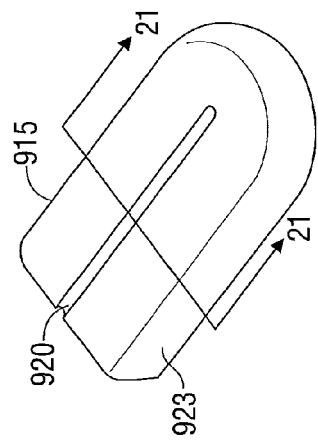
FIG. 20 is a perspective view of an example seal plate adapted for use in a method of manufacturing a jaw member in accordance with the present disclosure.
Figure 17:
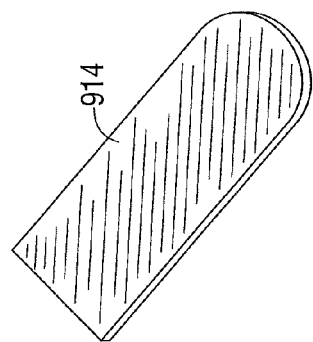
FIG. 17 illustrates an example seal plate blank adapted for use in a method of manufacturing a jaw member in accordance with the present disclosure.
Figure 19:
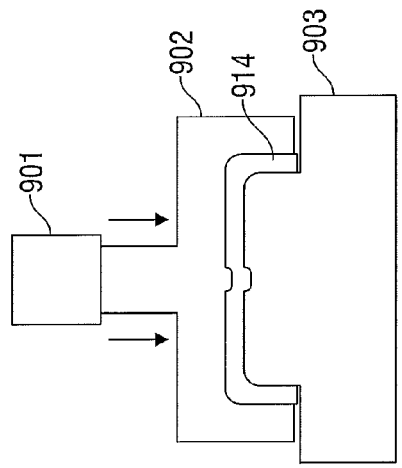
FIG. 19 illustrates an example step of a method of manufacturing a jaw member in accordance with the present disclosure wherein a forming die forms a seal plate blank into a seal plate.
Figure 21:
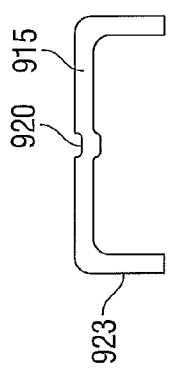
FIG. 21 is a cross-sectional view of an example seal plate adapted for use in a method of manufacturing a jaw member in accordance with the present disclosure.

An example method of manufacturing the various jaw members described hereinabove is now described with reference to FIGS. 17-28 and FIGS. 35-40. A seal plate blank 914, which may be formed by any suitable manner, e.g., stamping via a blanking die, is provided in FIG. 17. Seal plate blank 914 is placed between forming dies 902, 903 in a die press 901, as depicted in FIG. 18. The die press 901 extends driving forming die 902 downward over blank 914 and forming die 903, which forms a raw seal plate 915 having desired features, e.g., side wall 923 and knife channel 920, as seen in FIGS. 20 and 21.

Figure 22:
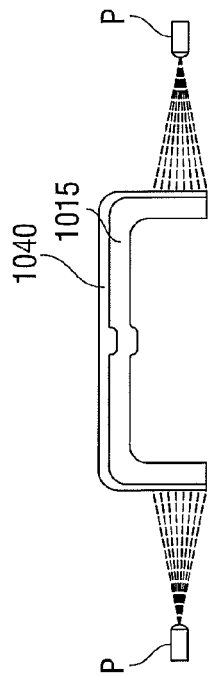
FIG. 22 is a cross-sectional view of an example seal plate having a photoresist coating and undergoing exposure in accordance with the present disclosure.

In FIG. 22, a raw seal plate 1015 is coated with a photoresist material 1040. In the present example, a positive photoresist 1040 is shown wherein exposure to light (typically ultraviolet light) or an electron beam provided by a photolithographic energy source P renders photoresist 1040 soluble to a photoresist developer. In other embodiments, a negative photoresist material may be employed wherein the non-exposed portions of coating 1040 are rendered soluble.

Figure 46:
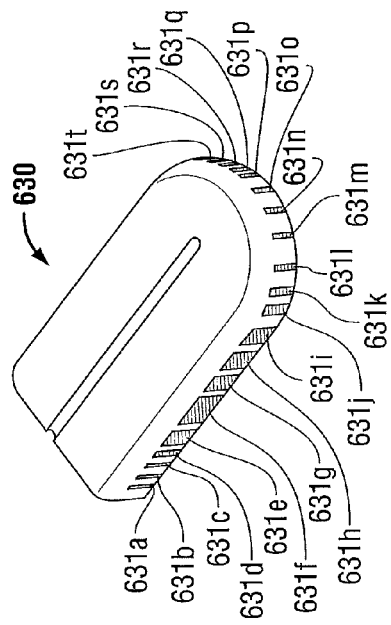
FIG. 46 is a perspective view of an additional example of a seal plate having a plurality of insulators of varying width in accordance with the present disclosure.
Figure 45:
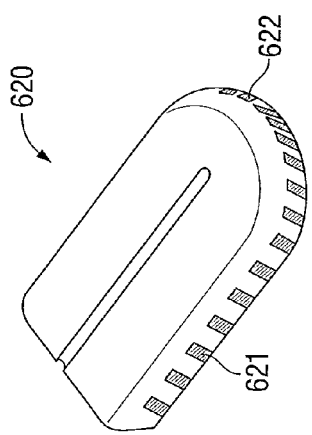
FIG. 45 is a perspective view of still another example seal plate having a plurality of insulators in a diagonal arrangement in accordance with the present disclosure.
Figure 47:
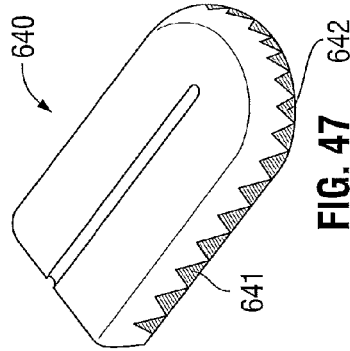
FIG. 47 is a perspective view of yet another additional example of a seal plate having a plurality of insulators having a sawtooth pattern in accordance with the present disclosure.

In the present positive photoresist example embodiment, energy source P exposes an area of photoresist 1040 corresponding to the desired insulation pattern, e.g., corresponding to groove 419 as shown in FIG. 29, notches 469 seen in FIG. 32, insulating regions 601a et seq. seen in FIG. 43, insulating regions 611, 612 as shown in FIG. 44, insulating regions 621 of FIG. 45, insulating regions 631 et seq. as seen in FIG. 46, insulating regions 641 of FIG. 47, and/or insulating regions 651 shown in FIG. 48.

Figure 24:
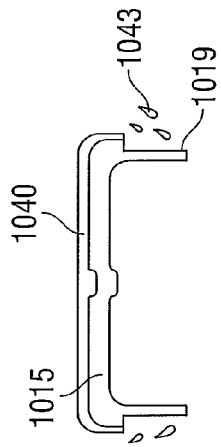
FIG. 24 is a cross-sectional view of an example seal plate undergoing etching in accordance with the present disclosure.
Figure 23:
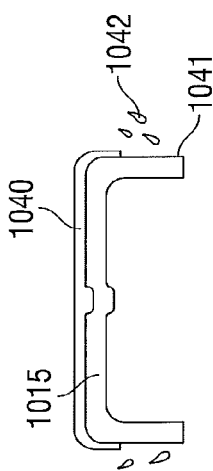
FIG. 23 is a cross-sectional view of an example seal plate undergoing photoresist developing in accordance with the present disclosure.
Figure 26:
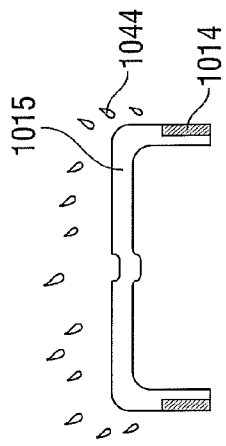
FIG. 26 is a cross-sectional view of an example seal plate undergoing photoresist removal in accordance with the present disclosure.
Figure 28:
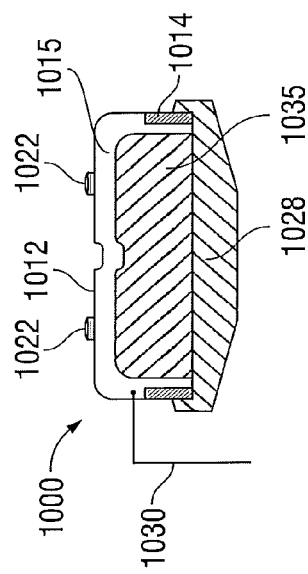
FIG. 28 is a cross-sectional view of an example seal plate with a second overmold in accordance with the present disclosure.
Figure 25:
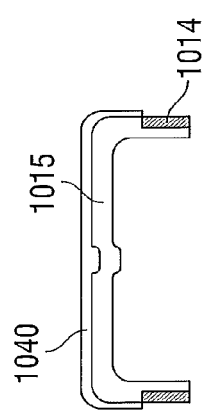
FIG. 25 is a cross-sectional view of an example seal plate undergoing insulation application in accordance with the present disclosure.

In FIG. 23, the exposed photoresist 1040 is developed by rinsing the photoresist coating 1040 with a developer solution 1042, resulting in a region 1041 of raw seal plate 1015 being revealed. In FIG. 24, an etchant solution 1043 is applied to the exposed portion 1041 of raw seal plate 1015 resulting in a notch 1019 being defined therein. In FIG. 25, the notch 1019 is filled, partially or completely, with an insulating material, e.g., polyimide. In FIG. 26, a rinsing or stripping solution 1044 is applied to the seal plate 1015 and the remaining photoresist 1040 is thereby removed.

Figure 27:
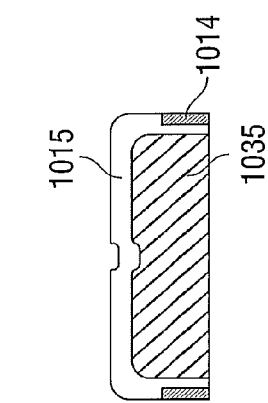
FIG. 27 is a cross-sectional view of an example seal plate with a first overmold in accordance with the present disclosure.

In the step illustrated in FIG. 27, an inner support 1035 is formed within seal plate 1015 by overmolding. In an embodiment, the inner support 1035 is formed from polyphthalamide thermoplastic polymer, e.g., Amodel®. In the step shown in FIG. 28, a jaw housing 1028 is overmolded to the bottom side of the seal plate 1015 and inner support 1035 combination formed in the FIG. 27 step, forming a jaw member 1000. See also FIGS. 31 and 34. Additionally, stop members 1022 may be fixed to a tissue-contacting surface 1012 seal plate 1015 by any suitable process, such as without limitation, overmolding. A conductor 1030 adapted to operably couple seal plate 1015 to a source of electrosurgical (e.g., sealing) energy may be fixed to seal plate 1015 by any suitable matter of attachment, including without limitation soldering, crimping, welding, brazing, and/or threaded fastener.

In another example method of manufacturing a jaw member 1100 in accordance with the present disclosure, in FIG. 35, a raw seal plate 1115 is coated with a photoresist material 1140. As in the prior example, a positive photoresist 1140 is shown. An energy source P exposes an area of photoresist 1040 corresponding to the desired insulation pattern, e.g., corresponding to the surface-mounted insulator 514 depicted in FIG. 41. In FIG. 36, the exposed photoresist 1140 is developed by rinsing the photoresist coating 1140 with a developer solution 1142, resulting in a region 1141 of raw seal plate 1115 being revealed. In FIG. 37, region 1141 is coated with an insulating material, e.g., polyimide, forming a surface-mounted insulating strip (see, e.g., FIG. 41). In FIG. 38, a rinsing or stripping solution 1144 is applied to the seal plate 1115 thereby removing any the remaining photoresist 1140 from seal plate 1115, leaving insulator 1114 disposed on side wall 1113 as can be readily appreciated.

In the step illustrated in FIG. 39, an inner support 1135 is formed within seal plate 1115 by overmolding. In an embodiment, the inner support 1135 is formed from polyphthalamide thermoplastic polymer. In the step shown in FIG. 40 a jaw housing 1128 is overmolded to the bottom side of the seal plate 1115 and inner support 1135 combination formed in the FIG. 39 step, forming a jaw member 1100. Additionally, stop members 1122 may be fixed to a tissue-contacting surface 1112 of seal plate 1115 by any suitable process, including without limitation overmolding. A conductor 1130 adapted to operably couple seal plate 1115 to a source of electrosurgical (e.g., sealing) energy may be fixed to seal plate 1115 by any suitable matter of attachment, including without limitation soldering, crimping, welding, brazing, and/or threaded fastener.

Figure 6:
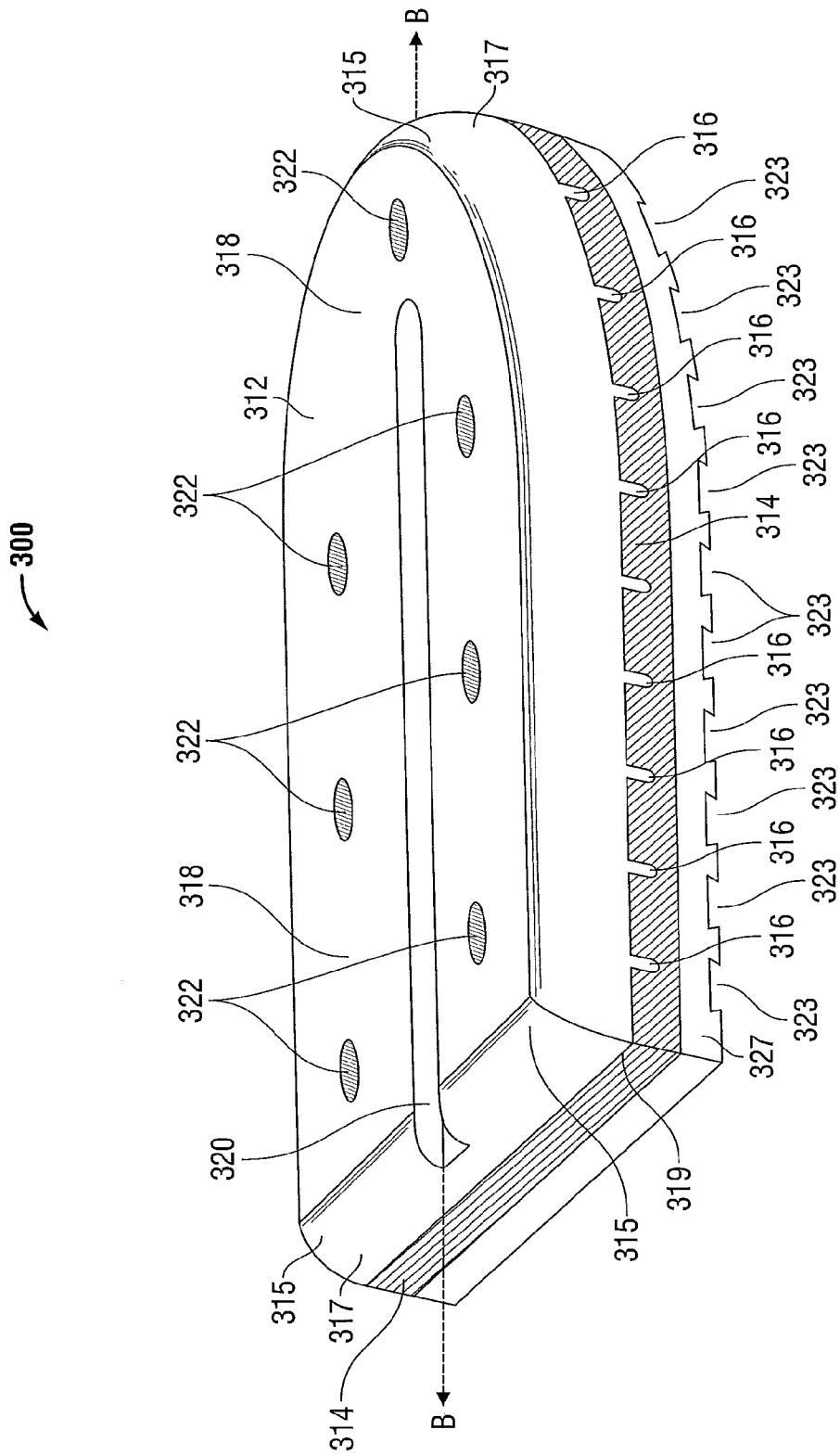
FIG. 6 is a perspective view of yet another example embodiment of a seal plate having a ribbed structure on a reverse surface thereof in accordance with the present disclosure.
Figure 7:
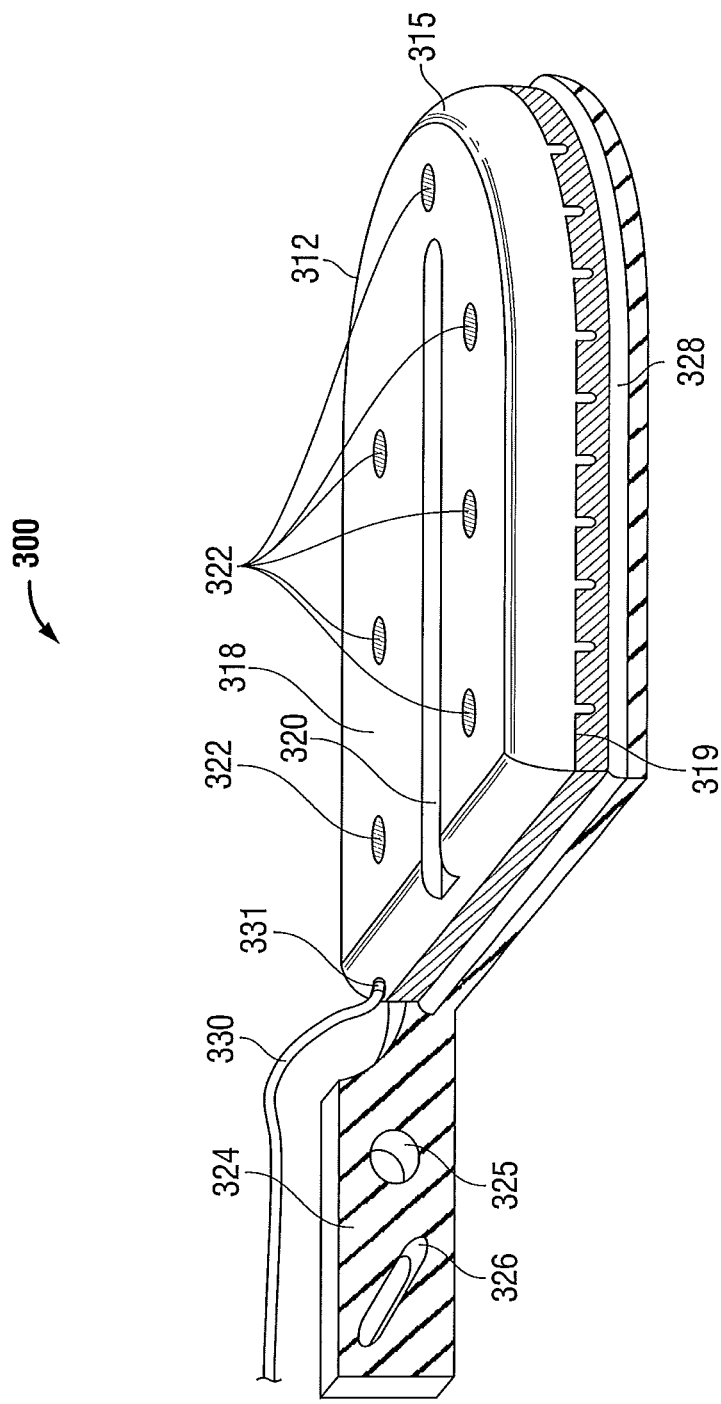
FIG. 7 is a perspective view of the FIG. 6 embodiment wherein a jaw housing is overmolded thereupon to form a jaw member in accordance with the present disclosure.
Figure 8:
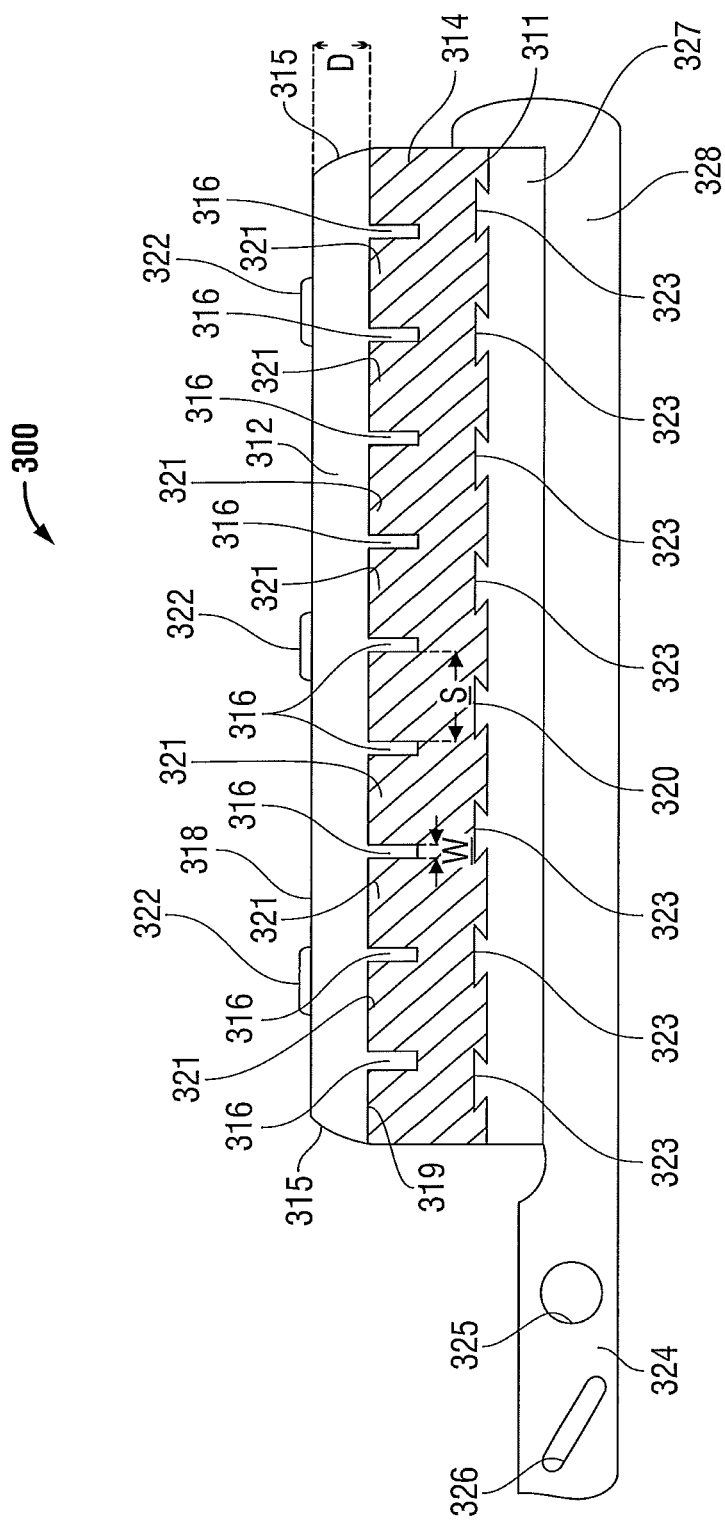
FIG. 8 is a side, cutaway view of the FIG. 6 embodiment of a vessel sealing jaw member in accordance with the present disclosure.
Figure 9:
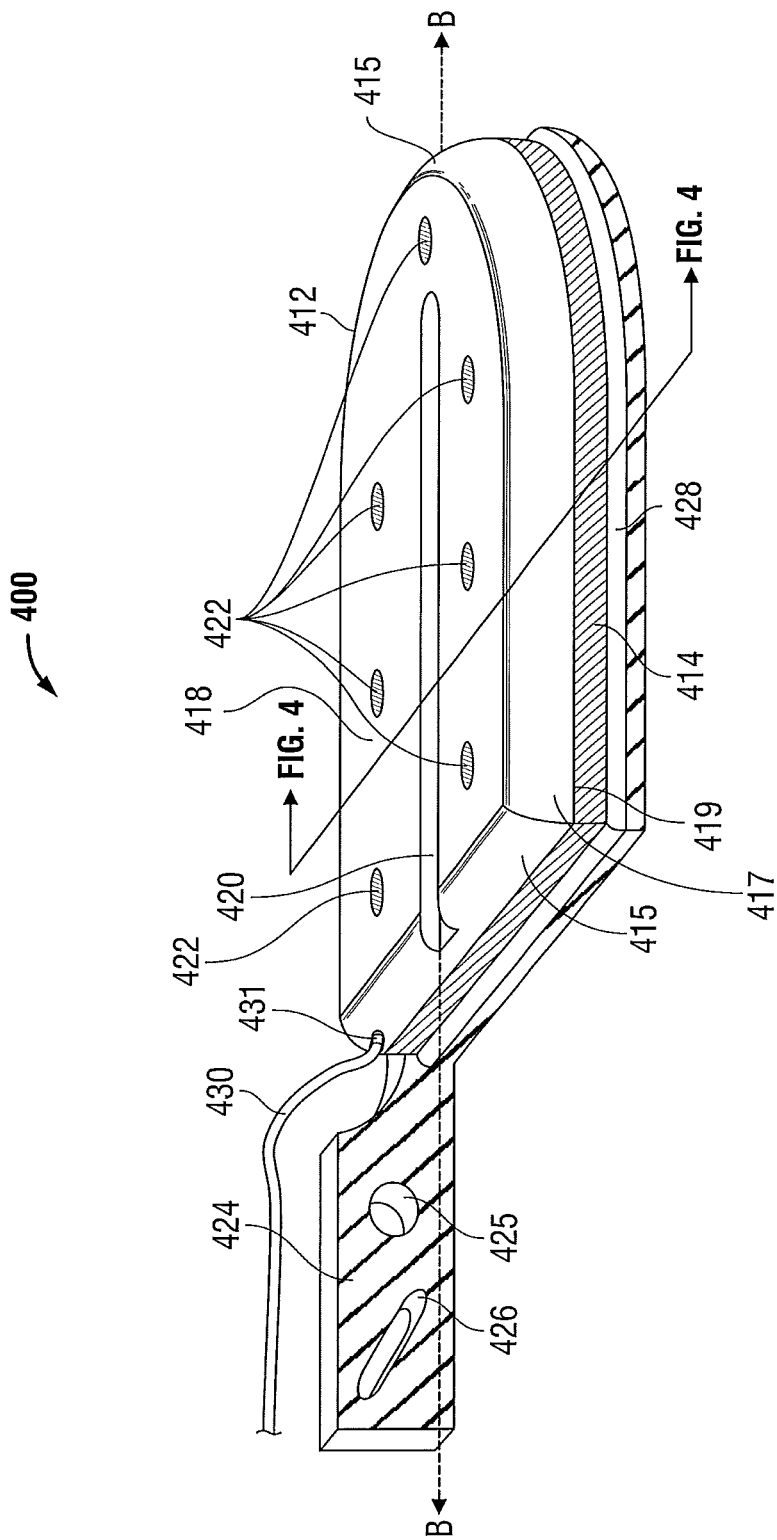
FIG. 9 is a perspective view of still another embodiment in accordance with the present disclosure wherein a jaw housing is overmolded thereupon to form a jaw member.

Turning now to FIGS. 6, 7, and 8, another example embodiment of a jaw member 300 in accordance with the present disclosure is described in detail. The described features of jaw member 300 is representative of one or more of the jaw members as described hereinabove (e.g., jaw members 110 and 120 of FIG. 1 and/or jaw members 210 and 220 of FIG. 2), and when included in an end effector assembly having opposing jaws (e.g., end effector assembly 130 of FIG. 1 and/or end effector assembly 230 of FIG. 2) include mutually corresponding component features that cooperate to permit rotation about a pivot pin (not explicitly shown) to effectively grasp, seal, and/or divide tissue.

Jaw member 300 includes an electrically conductive electrode or seal plate 312 and an insulating substrate or insulator 314. Insulator 314 is configured to securely engage electrode 312. This may be accomplished by, e.g., stamping, by overmolding, by overmolding a stamped electrically conductive sealing plate and/or by overmolding a metal injection molded seal plate. Insulating substrate 314, seal plate 312, and the outer, non-conductive jaw housing 328 (see FIG. 7) are configured to limit and/or reduce many of the known undesirable collateral effects related to tissue sealing, e.g., thermal spread and edge cutting.

Electrode 312 may also include an outer peripheral edge 317 that has a radius 315. In this embodiment insulator 314 meets electrode 312 along an adjoining edge that is generally tangential to the radius and/or meets along the radius. At the interface, electrode 312 is raised, e.g., more obverse, relative to insulator 314.

Seal plate 312 includes one or more ribs 316 extending from a reverse surface or underside 319 thereof. As shown in the example embodiment of FIGS. 6, 7, and 8, ribs 316 are substantially straight and oriented transverse to a longitudinal axis "B-B" of the jaw member 300. In other envisioned embodiments, ribs 316 may oriented longitudinally or at any angle with respect to a longitudinal axis "B-B" of the jaw member 300. Ribs 316 may define a path that includes circular, undulating, sawtooth, stepped, crosshatched, zigzag, or other shape path. As shown in the Figures, ribs 316 have a width to spacing (W:S) ratio of about 1:5; however, the W:S ratio may range from 1:100 to about 100:1. A plurality of ribs 316 may have a similar widths "W" or dissimilar widths "W". In some embodiments, the width "W" of successive ribs 316 may increase, decrease, or vary according to a pattern. The spacing "S" of the valleys 321 (see FIG. 8) formed between ribs 316 may be similar or dissimilar, and may increase, decrease, or vary according to a pattern. The effective depth "D" of seal plate 312 may range from about 0.001" to about 0.25", and in an embodiment may be about 0.013".

Insulating layer 314 is disposed on a reverse surface 319 of seal plate 312. Insulating layer 314 may be formed from any suitable temperature-resistant material having electrical and/or thermal insulating properties, including without limitation polyimide. As shown in FIGS. 6, 7, and 8, insulating layer 314 conforms to the ridges 316 and/or valleys of seal plate 312. Insulating layer 314 may be formed by any suitable manner of fabrication, including without limitation, overmolding, backfilling, and conformal coating. During use in a vessel sealing procedure, it is believed the combination of ribs 316 and insulating layer 314 together with radius 315 acts to control current paths within seal plate 312, which, in turn, reduces thermal spread and reduced edge cutting while optimizing the delivery of sealing energy to vessel tissue.

A backing plate 327 may be fixed to a reverse surface or underside 311 of insulating layer 314. Backing plate 327 may include one or more adhesion-enhancing features 323 that promote bonding between backing plate 327 and insulation layer 314. As shown, adhesion-enhancing features 323 include an interlocking dovetail arrangement; however any suitable texturing or surface features may be advantageously employed, including without limitation grooves, ribs, rod-like protrusions, and the like. Backing plate 327 may be formed from any suitable high-temperature metallic or non-metallic material, and in an embodiment, a material having dielectric properties differing from that of insulating layer 314 may be employed to further control current concentrations and thermal spread during vessel sealing procedures.

As mentioned above, jaw member 300 includes a jaw housing 328 that supports the combination of seal plate 312 and insulating layer 314, and, optionally, backing plate 327. In some embodiments, jaw housing 328 may be formed from non-conductive material, such as without limitation, high-strength ceramic material, and may be formed by overmolding. Jaw housing 328 may include a number of features designed to facilitate the mounting thereof on an instrument, e.g., a hinge plate 324 extending from a proximal end thereof. (See FIGS. 7 and 8.) The hinge plate 324 may include additional features adapted to pivot, mount, and articulate jaw member 300, including without limitation, pivot hole 325 and/or cam slot 326. A conductor (not explicitly shown) operably couples seal plate 312 to a source of vessel sealing energy, e.g., generators 20, 228.

A cable or wire 330 is electromechanically joined to seal plate 312 to facilitate the delivery of electrosurgical energy thereto. Wire 330 may be joined to seal plate 312 at junction 331 by any suitable manner of electromechanical coupling, including without limitation, crimping, soldering, welding, brazing, backstab connector, and the like. As shown, junction 331 is located in proximity to hinge plate 324 to facilitate routing of wire 330 proximally though the instrument. A proximal end of wire 330 (not explicitly shown) may be adapted to operably couple with a source of electrosurgical energy.

Figure 11:
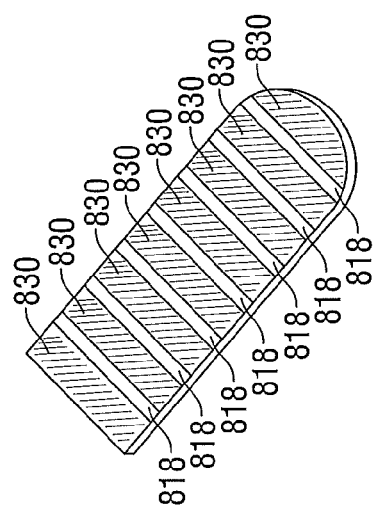
FIG. 11 illustrates an example step of a method of manufacturing a jaw member in accordance with the present disclosure wherein a resist mask is applied to a seal plate blank.
Figure 10:
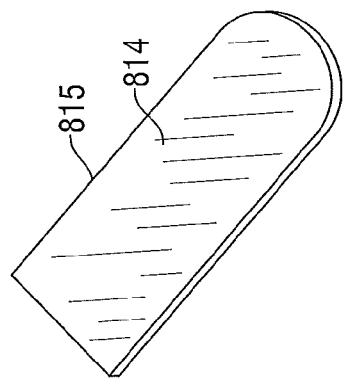
FIG. 10 illustrates an example step of a method of manufacturing a jaw member in accordance with the present disclosure wherein a seal plate blank is provided.

Ribs 316 may be formed by any suitable manner of manufacture, including without limitation, molding, stamping, machining, water jet cutting, or photolithography. An example embodiment of a fabrication method in accordance with the present disclosure is illustrated in FIGS. 10-16. A blank seal plate 815 having a reverse surface or underside 814 is provided as shown in FIG. 10. In FIG. 11, a resist mask 830 is applied to reverse surface 814 of seal plate 815 to expose regions 818. Regions 818 are etched to form valleys 821, and, correspondingly, those areas of reverse surface 814 protected by resist mask 830 form ribs 816.

Figure 12:
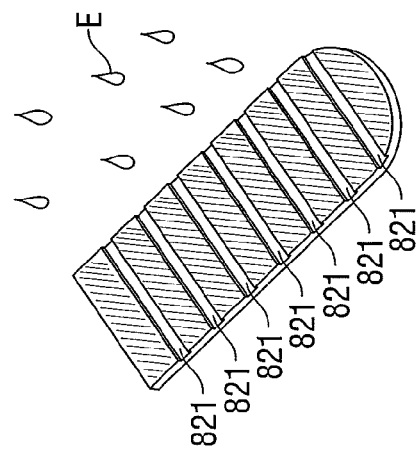
FIG. 12 illustrates an example step of a method of manufacturing a jaw member in accordance with the present disclosure wherein an etchant is applied to a seal plate blank.

As shown in FIG. 12, an etchant E is utilized to etch the desired series of valleys 821. In the step exemplified in FIG. 13, a rinsing agent R is applied to remove any remaining etchant and/or to remove resist mask 830, exposing the finished seal plate 815 having the desired series of ribs 816 and valleys 821. In the step exemplified in FIG. 14, an insulating layer 819 is applied to reverse surface 814 of seal plate 815 to form a seal plate subassembly 817. In some embodiments, insulating layer 819 is formed from polyimide by overmolding. Optionally, as shown in FIG. 15, the upper portion of insulating layer 819 may be etched, machined, or otherwise removed thereby leaving insulation 819' disposed only within each valley 821. An electrically conductive wire 830 is joined to seal plate 815 at junction 831. Wire 830 may be joined to seal plate 815 by any suitable manner of fixation, including without limitation, crimping, soldering, welding, brazing, backstab connector, and the like. In the step exemplified in FIG. 16, a jaw housing 828 is joined to seal plate subassembly 817 to form a jaw member 800. Jaw housing 828 may be joined to seal plate subassembly 817 by overmolding, by adhesive bonding, by mechanical coupling (e.g., threaded fastener, interlocking clips, or tabs), or by any suitable manner of fixation.

In some embodiments, jaw housing 828 is formed from non-conductive material, such as without limitation, high-strength ceramic material, or high-strength thermosetting polymeric material. Jaw housing 828 may be formed by e.g., overmolding, powder molding, injection molding, machining, stamping, or casting. Jaw housing 828 may include a number of features designed to facilitate the mounting thereof on an instrument, e.g., a hinge plate 824 having defined therein a pivot hole 825 and/or a cam slot 826.

Referring now to FIG. 6, in order to achieve the necessary gap range (e.g., about 0.001" to about 0.006") between opposing jaw members 110, 120 or 210, 220 to properly seal tissue, a jaw member 300 may include one or more stop members 322 that limit the movement between jaw members to within the specified range. Each stop member 322 is made from an insulative material and is dimensioned to limit opposing movement of jaw members to within the above gap range.

Seal plate 312 may be formed from any suitable temperature-resistant, electrically conductive material, such as without limitation, stainless steel. The tissue-contacting surface 318 of seal plate 312 may include an electrically-conductive lubricious coating (not explicitly shown) formed from, e.g., graphite-impregnated polytetrafluoroethylene (PTFE), mica-impregnated PTFE, metal-impregnated ceramic, or titanium nitride. The lubricious coating may reduce the tendency of vessel walls and/or other targeted tissue from undesirably adhering to seal plate 312.

A knife channel 320 may be defined through the center of jaw member 300 such that a knife having a distally-facing cutting edge (not explicitly shown) may cut through tissue T grasped between opposing jaw members, e.g., jaw members 110, 120 and/or jaw members 210, 220 when such jaw members are in a closed position. Details relating to the knife channel 320, trigger 240 (see FIG. 2), knife and a knife actuation assembly associated therewith (not shown) are explained in limited detail herein and explained in more detail with respect to commonly-owned U.S. Pat. Nos. 7,156,846 and 7,150,749 to Dycus et al.

Figure 49:
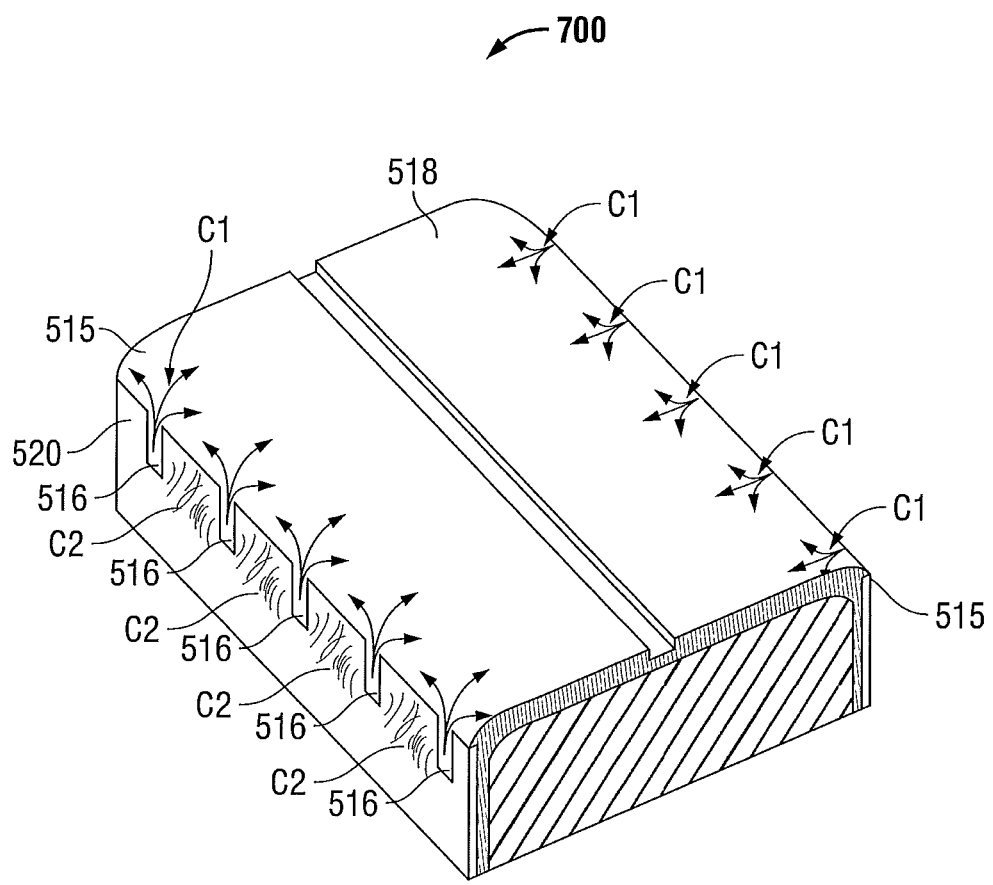
FIG. 49 illustrates current flows within an example embodiment of a jaw member in accordance with the present disclosure.

FIG. 49 depicts current flows "C1" and current concentrations "C2" within an embodiment of a jaw member 500 during use in accordance with the present disclosure. During use in a vessel sealing procedure, the combination of ribs 516 and insulating layer 514 together with radius 515 may act to control current flows C1 to generally within seal plate 512. As illustrated, current flows C1 radiate generally from ribs 516 toward tissue-contacting surface 518 along the edge radius 515 of seal plate 512. It is believed that the combination of edge radius 515 and ribbed structure 516 promotes surface current flows C1 away from side wall 520 of jaw member 500 and instead directs current flow along and across edge radius 515 and tissue-contacting surface 518, which, in turn, reduces edge cutting of tissue around the perimeter of the seal plate 512. It is also believed that, by directing energy away from side wall 520 in the manner just described, thermal spread may be reduced within tissue in the region the surrounding side wall 520, and surrounding jaw member 500 generally.

In another aspect, it is believed that during use, current concentrations C2 form in a region generally surrounding ribs 516, and reduces or eliminates lateral propagation of electrosurgical energy from side walls 520 of jaw member 500 into surrounding tissue. In turn, the decreased sideward propagation of electrosurgical energy results in corresponding decrease of thermal spread to the untargeted, peripheral areas of tissue, while simultaneously concentrating electrosurgical energy to regions of tissue disposed between the tissue contacting surface 518 of jaw member 500. In this manner, vessel sealing procedures may be performed with greater efficiency, with improved controllability and energy delivery and predictability of outcome, and ultimately lead to improved outcomes and decreased recovery times. Edge cutting may also be abated by the described mechanism of reducing lateral energy propagation, since the reduction of lateral energy impinging into surrounding tissue contributes to the overall reduction of unwanted build-up of thermal energy in surrounding tissue.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of manufacturing a jaw member, comprising the steps of:
    forming a raw seal plate having a tissue contacting surface and a side wall;
    applying photoresist material to at least a portion of the raw seal plate to form a coating;
    exposing a portion of the coating corresponding to an insulating region to an energy source;
    developing the coating to reveal a region of the side wall corresponding to the insulating region;
    applying insulating material to the region of the side wall corresponding to the insulating region;
    removing the coating from the raw seal plate; and
    forming a jaw housing to a bottom side of the raw seal plate and at least a part of the insulating region.

2. The method of manufacturing a jaw member in accordance with claim 1, wherein the forming step is performed by overmolding.

3. The method of manufacturing a jaw member in accordance with claim 1, further comprising the step of forming a recessed region in the side wall corresponding to the insulating region.

4. The method of manufacturing a jaw member in accordance with claim 1, wherein the recess is formed by applying an etchant to the region of the side wall corresponding to the insulating region.

5. The method of manufacturing a jaw member in accordance with claim 1, wherein the insulating material is applied to the recessed region.

6. The method of manufacturing a jaw member in accordance with claim 1 wherein the energy source is a photolithographic energy source.

7. The method of manufacturing a jaw member in accordance with claim 6, wherein the photolithographic energy source is selected from the group consisting of ultraviolet light source and an electron beam source.

* * * * *